(12) United States Patent
Tremont et al.

(10) Patent No.: US 6,413,945 B1
(45) Date of Patent: Jul. 2, 2002

(54) GASTRO-SPECIFIC PRODRUGS

(75) Inventors: Samuel J. Tremont, Manchester, MO (US); Paul W. Collins, Grayslake; Ricky L. Fenton, Collinsville, both of IL (US)

(73) Assignee: Pharmacia Corporation, Peapack, NJ (US)

( * ) Notice: Subject to any disclaimer, the term of this patent is extended or adjusted under 35 U.S.C. 154(b) by 0 days.

(21) Appl. No.: 09/514,819

(22) Filed: Feb. 28, 2000

Related U.S. Application Data

(63) Continuation-in-part of application No. 09/049,992, filed on Mar. 30, 1998, now Pat. No. 6,030,959.
(60) Provisional application No. 60/042,640, filed on Apr. 4, 1997.

(51) Int. Cl.$^7$ .......................... C07F 7/10; A61K 31/695
(52) U.S. Cl. .......................................... 514/63; 556/418
(58) Field of Search .............................. 514/63; 554/418

(56) References Cited

U.S. PATENT DOCUMENTS 6,030,959 A * 2/2000 Tremont ...................... 514/63

* cited by examiner

*Primary Examiner*—Robert Gerstl
(74) *Attorney, Agent, or Firm*—Fitzpatrick, Cella, Harper & Scinto

(57) ABSTRACT

A compound is disclosed havin the formula $$AW-SiR^1R^2R^3$$

wherein $R^1$ and $R^2$ are independently alkyl, cycloalkyl, alkenyl, alkynyl, aryl, aralkyl, alkaryl, or a hydrophilic group; $R^3$ is a hydrophilic group; and AW is the covalently bonded form of a drug AWH, wherein W is O, NH, S, or an enolate group. The hydrophilic group may be either non-neutral, or may be a polyol. This compound serves as a prodrug for the drug AWH. A method for preparing these compounds is also disclosed. Also disclosed is a method of treatment or prevention of gastric ulcers by administering the prodrug compounds.

28 Claims, No Drawings

GASTRO-SPECIFIC PRODRUGS

This application is a continuation-in-part of U.S. patent application Ser. No. 09/049,992, filed Mar. 30, 1998, now U.S. Pat. No. 6,030,959 which claims the benefit of U.S. Provisional Application No. 60/042,640, filed Apr. 4, 1997.

BACKGROUND OF THE INVENTION

1. Field of the Invention

This invention relates to silyl ether prodrugs containing at least one hydrophilic group on the silicon atom. The prodrugs hydrolyze at low pH, enabling release of the active drug in the gastric pH range. The invention further relates to a method of preparation of the silyl ether prodrugs, and to a method of treatment or prevention of gastric ulcers with a prodrug of misoprostol.

2. Related Background Art

It is known in the art that trialkylsilyl ether groups can be employed in pH-selective delivery systems for drug molecules. J. Chem. Soc. Perkin Trans., Vol. 10, p. 3043 (1992); J. Pharm. Sci., Vol. 77, p. 116 (1988); Int. J. Pharm., Vol. 28, p. 1 (1986); J. Pharm. Sci., Vol. 71, p. 1 (1982); Scientia Pharmaceutica, Vol. 43, p. 217 (1975); and JP 8,165,301. In these references, prodrugs containing trialkylsilyl ethers were formed from hydroxyl-containing drugs and found to undergo hydrolysis to release the drug only at low pH values. Such systems are of particular interest for selective delivery of drugs to the stomach, where pH values are typically in the range from 1 to 4. When any remaining prodrug passes into the intestine, where pH values are typically about 7, release of the drug ceases, thus avoiding the side effects usually associated with intestinal absorption.

Trialkylsilyl ethers formed at one or more of the hydroxyl groups of drugs in the prostaglandin series are also well known. In U.S. Pat. No. 3,965,143, a triethylsilyl ether is formed at position 16 of misoprostol, a prostaglandin drug. In U.S. Pat. Nos. 5,055,604 and 5,075,478, and in ES 545634, the 11-triethylsilyl ether of misoprostol is formed. U.S. Pat. No. 5,252,763 discloses a process for making a trialkylsilyl ether, in which the alkyl groups contain from 1 to 6 carbon atoms, at the 11 position of misoprostol. Finally, PCT Application No. WO 96/28419 discloses a trialkylsilyl ether at the 11 position, in which the alkyl groups contain from 1 to 8 carbon atoms. In all of the aforementioned references, the trialkylsilyl ethers are disclosed only as intermediates in the synthesis of prostaglandins. No suggestion is made that these compounds would be useful as delivery systems for prostaglandins, or that hydrophilic groups be substituted for the alkyl groups in the trialkylsilyl ether.

A polymeric delivery system in which a drug, such as a prostaglandin, is covalently bonded through a hydroxyl substituent, and is selectively released at a predetermined pH is described in PCT Application No. WO 92/01477; U.S. Pat. No. 5,474,767; and Journal of Medicinal Chemistry, Vol. 36, p. 3087 (1993). The pH-selective drug delivery systems described in these references comprise a drug covalently bonded to a linker by reaction with a silyl chloride functional group on the linker, thus forming an acid-sensitive silyl ether bond, and a polymer which is covalently bonded to the linker-drug combination. The polymer is crosslinked following bonding of the linker, or in some cases, prior to bonding of the linker. In an acidic environment, the silyl ether bonds hydrolyze, allowing the drug molecules to diffuse from the polymer matrix. However, unlike many prodrugs, the polymer-bound drug has no significant hydrophilic nature. No suggestion is made in these references to attach a hydrophilic group to the drug.

SUMMARY OF THE INVENTION

This invention provides a compound of the formula

$$AW\text{---}SiR^1R^2R^3$$

wherein $R^1$ and $R^2$ are independently alkyl, cycloalkyl, alkenyl, alkynyl, aryl, aralkyl, alkaryl, or a hydrophilic group; $R^3$ is a hydrophilic group; and AW is the covalently bonded form of a drug AWH, wherein W is O, $CO_2$, NH, S, or an enolate group. Of course, each of $R^1$, $R^2$ or $R^3$ or all may independently contain hydrophilic groups. The hydrophilic group may be non-neutral, or may be a polyol. In a most preferred embodiment the hydrophilic group is a tertiary amine or polyethylene glycol. This compound serves as a prodrug for the drug AWH.

This invention also provides a method for preparing these compounds by first reacting the drug AWH with a compound of formula

$$YSiR^1R^2R^7$$

wherein Y is halo, or an alkyl-, haloalkyl-, aryl-, alkaryl-, aralkyl-, or haloaryl- sulfonate ester; $R^1$ and $R^2$ are as previously described; $R^7$ is a group substituted by a halo group. The product of this first step is reacted with either (1) a compound containing at least one amino group or (2) a polyol. In a preferred embodiment, the product of the first step is reacted with a compound containing at least one tertiary amine. In another preferred embodiment, the product of the first step is reacted with an amine-substituted polyol, or an alkylamine of twenty carbons or less which can then be further reacted with a transformed polyol to provide an amine-substituted polyol. In another preferred embodiment, the product of the first step can be reacted with an unmodified polyol which may optionally be transformed and then reacted with a tertiary amine. In a preferred embodiment, the polyols of this invention are polyethylene glycol (PEG).

This invention also provides a method of treatment or prevention of gastric ulcers by administering the prodrug compounds of this invention.

DETAILED DESCRIPTION OF THE INVENTION

The following terms used herein are defined. The term "THF" indicates the solvent tetrahydrofuran. The term "DMF" indicates the solvent N,N-dimethylformamide. The term "mercapto" refers to the substituent moiety SH, bonded through its sulfur atom to a carbon atom on a substrate. The term "alkyl" refers to a straight or branched alkyl group containing from 1 to 20 carbon atoms. The term "alkenyl" refers to a straight or branched hydrocarbon group containing from 1 to 20 carbon atoms and at least one carbon-carbon double bond. The term "alkynyl" refers to a straight or branched hydrocarbon group containing from 1 to 20 carbon atoms and at least one carbon-carbon triple bond. The term "cycloalkyl" refers to a cyclic alkyl group containing up to 20 carbon atoms. The term "aryl" refers to a substituent derived from a cyclic aromatic compound having up to 20 carbon atoms. The term "aralkyl" refers to an alkyl group substituted by an aryl group. The term "alkaryl" refers to an aryl group substituted by an alkyl group. The term "halo" means a fluoro, chloro, bromo, or iodo group. The term "Ph" refers to a difunctional phenylene moiety substituted at the 1 and 4 positions. The term "polyol" refers to polyhydroxyl-containing compounds, containing 2 or more hydroxyl moieties, preferably on a carbon backbone which may be substituted by oxygen. Exemplary polyol compounds include, but are not limited to, glycols, e.g., ethylene glycol, propylene glycol; polyglycols, e.g.,PEG, polypropylene glycol; and polyhydric alcohols.

The term "transform" refers to the reaction by which a hydroxyl group on a polyol has been substituted with a leaving group, and the term "transformed polyol" refers to a polyol which has been thus reacted. Polyols may be transformed by reaction with tosylate, mesylate, triflate or other methods well-known in the art. The term "unmodified polyol" refers to a polyol which has not been transformed.

The prodrug compounds of this invention have the general formula

AW—SiR$^1$R$^2$R$^3$ wherein R$^1$ and R$^2$ are independently alkyl, cycloalkyl, alkenyl, alkynyl, aryl, aralkyl, alkaryl, or a hydrophilic group; R$^3$ is a hydrophilic group; and AW is the covalently bonded form of a drug AWH, wherein W is O, CO$_2$, NH, S or an enolate group. Each of R$^1$, R$^2$ or R$^3$ or all may independently contain hydrophilic groups. The hydrophilic group may be non-neutral, or may be a polyol. The AW-Si bond in these molecules is susceptible to hydrolysis at low pH values. Hydrolysis of the AW-Si bond releases the drug AWH from the prodrug when the prodrug reaches the low-pH environment of the stomach. Conversely, any remaining prodrug which passes into the higher-pH environment of the intestines will no longer release the drug, thereby avoiding the side effects usually associated with intestinal release.

Preferably, R$^1$ and R$^2$ are independently alkyl, cycloalkyl, alkenyl, alkynyl, aryl, aralkyl, alkaryl, or polyol, and R$^3$ is a group comprising at least one quaternary ammonium salt or a polyethylene glycol, making R$^3$ a hydrophilic group that is non-neutral or a polyol.

If R$^3$ contains two, three, or four amino groups or quaternary ammonium salt groups, the prodrug may contain two, three, or four AWSiR$^1$R$^2$ groups, respectively. Moreover, more than one type of drug AW may be released from this multiple prodrug system. Typically, R$^3$ will be a group with the formula

—L—(NR$^4$R$^5$R$^6$)$^+$X$^-$ wherein X$^-$ is a halide ion or any pharmaceutically acceptable anion; L is a difunctional alkyl, alkenyl, or alkynyl group, a polyol, or a group with the formula

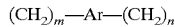
(CH$_2$)$_m$—Ar—(CH$_2$)$_n$ wherein Ar is a difunctional aryl or cycloalkyl group, m is an integer from 0 to 3 inclusive, and n is an integer from 0 to 2 inclusive; R$^4$ and R$^5$ are independently alkyl, alkenyl, alkynyl or polyol; and R$^6$ is alkyl, alkenyl, alkynyl, polyol, or a group with the formula

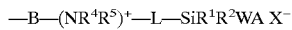
—B—(NR$^4$R$^5$)$^+$—L—SiR$^1$R$^2$WA X$^-$ wherein B is a difunctional alkyl, alkenyl, alkynyl group, a polyol, or a group with the formula

(CH$_2$)$_j$—Ar—(CH$_2$)$_k$ wherein j is an integer from 0 to 3 inclusive, and k is an integer from 0 to 3 inclusive.

The compound of this invention will be a dimer if, in the aforementioned definition of R$^3$, the choice for R$^6$ is a group with the formula

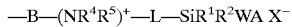
—B—(NR$^4$R$^5$)$^+$—L—SiR$^1$R$^2$WA X$^-$

With this choice for R$^6$, the resulting dimeric structure of the compound will be

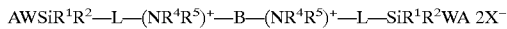
AWSiR$^1$R$^2$—L—(NR$^4$R$^5$)$^+$—B—(NR$^4$R$^5$)$^+$—L—SiR$^1$R$^2$WA 2X$^-$ As previously noted, in an alternative embodiment, AW may be more than one type of drug.

Most preferably, R$^1$ and R$^2$ are independently alkyl or aryl, and R$^3$ is a group of the formula

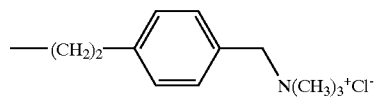

This represents the choice of L as a group with the formula

(CH$_2$)$_m$—Ar—(CH$_2$)$_n$ wherein Ar is a 1,4-phenylene group, m is 2, n is 1; R$^4$, R$^5$ and R$^6$ are all methyl; and X$^-$ is Cl$^-$.

Hydroxyl-containing drugs, i.e. AOH, are most preferred for incorporation into the compound of this invention, especially those wherein gastric release, at a typical gastric pH value between 1 and 4, is preferred over intestinal release, or wherein control of the rate of release is desired for systemic action. For example, drugs for which delivery to the stomach is preferred include natural or synthetic prostaglandins and prostacyclins (e.g., misoprostol, enisoprost, enprostil, iloprost, and arbaprostil), any drugs for treatment or prevention of peptic ulcers, gastric antisecretory drugs, antimicrobial drugs, prokinetic drugs, cytoprotective drugs and the like. Exemplary antimicrobial drugs include tetracycline, metronidazole and erythromycin which can be used for the eradication of gastric microbes. The most preferred drug for use in the prodrug of this invention is misoprostol.

This invention also includes a method for making the prodrug by first reacting the drug AWH with a compound of formula

YSiR$^1$R$^2$R$^7$ wherein Y is halo, or an alkyl-, haloalkyl-, aryl-, alkaryl-, aralkyl-, or haloaryl- sulfonate ester; R$^1$ and R$^2$ are as previously described; R$^7$ is a group substituted by a halo group. The product of this first step is reacted with either (1) a compound containing at least one amino group or (2) a polyol. In a preferred embodiment, the product of the first step is reacted with a compound containing at least one tertiary amine. In another preferred embodiment, the product of the first step is reacted with an amine-substituted polyol, or an alkylamine of twenty carbons or less which can then be further reacted with a transformed polyol to provide an amine-substituted polyol. In another preferred embodiment, the product of the first step can be reacted with a polyol which may optionally be transformed and then reacted with a tertiary amine. In a preferred embodiment, the polyols of this invention are polyethylene glycol (PEG).

In a preferred embodiment of this invention, a drug AWH is first reacted with a compound of the formula

YSiR$^1$R$^2$R$^7$ wherein $R^7$ is a group of the formula —L—X, or a group of the formula

to form a compound of formula $AWSiR^1R^2R^7$, wherein Y, $R^1$, $R^2$, and L are as previously described and X is halo. This first step couples the drug with a substituted silane to form a silyl ether, silyl ester, silyl amide, silyl thioether, or silyl enol ether.

In a second step, the silyl ether product of the first step is then reacted with either (1) a compound containing at least one amino group or (2) a polyol.

In a preferred embodiment of the second step, the compound containing at least one amino group is represented by the formula $Z(NR^4R^5)_p$, wherein $R^4$ and $R^5$ are independently hydrogen, alkyl, alkenyl, alkynyl or polyol; Z is hydrogen, alkyl, alkenyl, alkynyl or polyol, and p is 1; or p is 2 and Z is a difunctional alkyl, alkenyl, or alkynyl group, a polyol, or a group with the formula

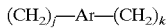

wherein j is an integer from 0 to 3 inclusive, and k is an integer from 0 to 3 inclusive. In this step, a halo substituent on one of the silyl substituents is displaced by an amino group. In a preferred embodiment, $R^4$ and $R^5$ are independently alkyl, alkenyl or alkynyl; Z is alkyl, alkenyl or alkynyl, and the halo substituent on one of the silyl substituents is displaced by a tertiary amine to produce a quaternary ammonium salt. The product of these transformations will be a dimer if p is 2 and Z is difunctional, i.e. if $Z(NR^4R^5)_p$ is a diamine. In such a case, the diamine will preferably displace a halo or sulfonate substituent from each of two molecules of the silyl starting material, thereby producing a symmetrical dimeric structure.

If the anion, $X^-$, produced by reaction of $R^7$ with an amino group, is not a pharmaceutically acceptable anion, any of the ion exchange methods well known in the art may be employed to replace the anion with one that is pharmaceutically acceptable.

In another preferred embodiment of the second step, the silyl ether product of the first step is reacted with an amine-substituted polyol containing at least one amino group. Preferably, the polyol is an amino or diamino polyethylene glycol represented by the formula $R^8(CH_2CH_2O—CH_2CH_2)_kNH_2$ wherein $R^8$ is an alkoxy, amino, hydroxyl or hydrogen group, and k is an integer in the range of 1–100, preferably 10–50. Amino or diamino polyethylene glycols are commercially available from Sigma-Aldrich Corp in St. Louis, Mo. or from Shearwater Polymers Inc. in Huntsville, Ala. The resulting amino-substituted polyol system will be polar as a result of the hydroxyl groups on the polyol, thus providing a useful hydrophilic character for pharmaceutical application.

This resulting amine-substituted polyol system can also be achieved by another route. Instead of reacting the silyl ether product of the first step with an amine-substituted polyol, the product is reacted with an alkylamine of twenty carbons or less. The alkylamine is then reacted with a transformed polyol to provide the same resulting amine-substituted polyol system described above. This alternate route may be commercially advantageous since unsubstituted polyol reagents are less expensive than amine-substituted polyols.

In yet another preferred embodiment, the silyl ether product of the first step can instead be reacted with a polyol, represented by the formula $R^8(CH_2CH_2O—CH_2CH_2)R^9$, wherein $R^8$ is as described above, $R^9$ is an alkoxy, amino or hydroxyl group, and k is as described above. While the resulting polyol system may be non-neutral, it is nonetheless polar and has useful hydrophilic character for pharmaceutical application. As an optional step, the resulting polyol system can be further modified by transforming a hydroxyl group on the polyol into a leaving group, and reacting the transformed polyol with a tertiary amine of the formula $Z(NR^4R^5)_p$, wherein Z, N, $R^4$, $R^5$ and p are described as above.

A preferred silyl chloride reactant for use in the method of this invention may be synthesized in a two-step process. The first step is introduction of a silyl moiety into an unsaturated substituent on a substrate which also bears a reactive halo substituent. This is preferably accomplished by catalytic hydrosilylation. Suitable substrates for this reaction include those having a carbon-carbon double bond which can undergo the hydrosilylation reaction, as well as a reactive halo substituent, such as the 4-vinylbenzyl halides. The most preferred substrate is 4-vinylbenzyl chloride. Preferred silanes for use in this reaction include the dialkylsilanes or alkylarylsilanes, such as dimethylsilane, methylethylsilane, diethylsilane, methylisopropylsilane, ethylisopropylsilane, diisopropylsilane, isobutylisopropylsilane, isobutylpropylsilane, isobutylethylsilane, isobutylmethylsilane, propylisopropylsilane, propylethylsilane, propylisobutylsilane, tert-butylmethylsilane, tert-butylethylsilane, tert-butylphenylsilane, tert-butylisopropylsilane, tert-butylisobutylsilane, and the like. The most preferred silanes are diisopropylsilane, tert-butylmethylsilane, and tert-butylphenylsilane. Preferred catalysts for promoting the hydrosilylation reaction include a variety of platinum and rhodium catalysts, such as platinum divinyltetramethyldisiloxane and tris(triphenylphosphine)rhodium(I) chloride ("Wilkinson's catalyst"). The most preferred catalyst is platinum divinyltetramethyldisiloxane. Preferred solvents for use in hydrosilylation may include any solvent which will dissolve the substrate and which will not undergo hydrosilylation. Examples are the aromatic hydrocarbon solvents such as toluene, any of the xylenes, and ethylbenzene, and aliphatic hydrocarbon solvents such as any of the pentanes, hexanes, heptanes, octanes, cyclohexane, cyclopentane, and the like, and mixtures thereof. The most preferred solvents are toluene and the xylenes, and mixtures thereof. The hydrosilylation reaction is preferably carried out at a temperature in the range from about 15° C. to about 120° C., most preferably from 50° C. to 80° C. Preferably, the reaction is allowed to proceed for a period of about 1 to about 24 hours, most preferably from 5 to 14 hours.

The second step in preparation of a preferred silyl chloride starting material is chlorination of the silane product of the first step. This is typically accomplished by treatment with a solution of chlorine gas in an organic solvent. Suitable solvents for this reaction include the halogenated solvents, such as chlorobenzene, 1,2-dichlorobenzene, dichloromethane, tetrachloromethane, chloroform, 1,2-dichloroethane, 1,1,1-trichloroethane, 1,1,2,2-tetrachloroethane, tetrachloroethylene, and the like. Preferred solvents are dichloromethane, 1,2-dichloroethane, and tetrachloromethane. The most preferred solvent is dichloromethane. The chlorination is typically carried out below room temperature, preferably below about −20° C., most preferably at about −78° C. Preferably, the reaction is allowed to proceed for a period of about 10 minutes to about 3 hours. The reaction mixture may be monitored using an analytical method capable of detecting the level of starting material, product, or both, such as gas chromatography. The reaction may be allowed to proceed until the starting material is substantially consumed.

The steps of hydrosilylation and chlorination in this preferred embodiment may effectively be combined by carrying out the hydrosilylation under the same conditions, but with a dialkylchlorosilane or alkylarylchlorosilane starting material rather than a dialkylsilane or alkylarylsilane starting material. For example, hydrosilylation of 4-vinylbenzyl chloride with a dialkylchlorosilane produces the desired 1-dialkylchlorosilyl-2-[4-(chloromethyl)phenyl] ethane directly.

In a preferred embodiment of this invention, the preferred silyl chloride starting material is coupled to the drug molecule. This is typically accomplished by combining the drug and the silyl chloride in a solvent. Suitable solvents for this step include those capable of dissolving the drug, but which are not reactive towards the silyl chloride functional group, including the polar aprotic solvents, such as N,N-dimethylformamide (DMF), THF, N,N-dimethylacetamide, N-methylpyrrolidone, 1,2-dimethoxyethane, and halogenated solvents such as chlorobenzene, 1,2-dichlorobenzene, dichloromethane, tetrachloromethane, chloroform, 1,2-dichloroethane, 1,1,1-trichloroethane, 1,1,2,2-tetrachloroethane, tetrachloroethylene, and the like. Preferred solvents are DMF, dichloromethane, and THF. The most preferred solvent is DMF. An additional compound may be added as a promoter for the coupling reaction, typically a nitrogen-containing compound.

Preferred promoters include imidazole and 4-dimethylaminopyridine. The most preferred promoter is imidazole. This reaction is preferably carried out at a temperature in the range from about 15° C. to about 100° C., most preferably from 20° C. to 40° C. Preferably, the reaction is allowed to proceed for a period of about 1 to about 18 hours. The progress of the reaction may be followed by using a method capable of detecting the level of starting material, product, or both, such as thin-layer chromatography or liquid chromatography. The reaction may be allowed to proceed until the starting material is substantially consumed.

Preferably, the coupled product described above is then reacted with any one of the following (1) a tertiary amine, (2) an amine-substituted polyol, (3) an alkylamine followed by a transformed polyol, or (4) an unmodified polyol, which may optionally be transformed and then reacted with a tertiary amine. Any of these four reactions is typically accomplished by combining the coupled product and the amine or polyol in a solvent. Suitable solvents for this step include the polar aprotic solvents such as THF, DMF, N,N-dimethylacetamide, N-methylpyrrolidone, 1,2-dimethoxyethane, and the like. The preferred solvents are DMF and THF. The most preferred solvent is THF. Preferably, this reaction is carried out at a temperature in the range from about 15° C. to about 75° C., most preferably from 20° C. to 40° C. Preferably, the reaction is allowed to proceed for a period of about 10 hours to about 3 days, most preferably from 18 hours to 2 days.

If the coupled product is reacted with compounds containing a polyol, then a catalyst may be added to the solvent. Recommended catalysts include, but are not limited to, potassium iodide, sodium iodide and tetrabutyl ammonium. Preferably, the catalyst should be added under temperature conditions that range from room temperature to 100° C.

If transformation of the polyol is required, one of the hydroxyl groups on the unmodified polyol may be transformed into a leaving group by reaction with tosylate, mesylate or triflate or by other methods well known in the art. The reaction is accomplished under temperature conditions that range from room temperature to 100° C. The transformed polyol can then be reacted with an amino group of an alkylamine or a tertiary amine as described above.

Reaction of the coupled drug product to polyols or their derivatives results in a drug delivery system with a substantially slower release rate. The release rate can be further controlled by the size of the polyol, with larger molecular weight polyols resulting in faster release rates. Biocompatible polyols such as PEGs offer other advantages in that they are soluble in both aqueous and organic solvents and are non-toxic, non-immunogenic and readily excreted. PEGs are commercially available in various molecular weights from such sources as Sigma-Aldrich Corp in St. Louis, Mo. or from Shearwater Polymers Inc. in Huntsville, Ala.

Another embodiment of this invention is directed to the method of treating or preventing gastric ulcers by administration of the prodrug of this invention. The active ingredient in this invention may be any substance that is desired for administration by selective release in an acidic environment, such as a drug, a sequestrant, or a ligand for complexation of metals. In each case, a suitable active ingredient will be one which forms a pH-sensitive covalent bond with a silyl compound. The active ingredient is substituted by a hydroxyl, carboxylate, amino, mercapto, or enolizable carbonyl group which is capable of reacting with a silyl compound to form a covalent bond. Preferably, the active ingredient is a hydroxy-containing biologically active material, e.g., a drug, intended to be administered orally, especially those wherein gastric release, at a typical gastric pH value between 1 and 6, is preferred over intestinal release, or wherein control of the rate of release is desired for systemic action. For example, drugs for which delivery to the stomach is preferred include natural or synthetic prostaglandins and prostacyclins (e.g., misoprostol, enisoprost, enprostil, iloprost, and arbaprostil), any other drugs for treatment or prevention of peptic ulcers, gastric antisecretory drugs, antimicrobial drugs, prokinetic drugs, cytoprotective drugs and the like. Preferred prostaglandin drugs which may be delivered by the prodrug of this invention are those described in PCT Application No. WO 92/01477, the disclosure of which is incorporated by reference herein. Exemplary antimicrobial drugs include tetracycline, metronidazole and erythromycin which can be used for the eradication of gastric microbes. The most preferred drug for delivery by the prodrug of this invention is misoprostol.

The preferred amount of prodrug to be administered is an amount that is sufficient to prevent, cure, or treat a condition for a desired period of time for which the delivery system of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the subject in which it is used, and the body weight of that subject. An effective amount is that amount which in a composition of this invention provides a sufficient amount of the active ingredient to provide the requisite activity of the active ingredient in the body of the treated subject for the desired period of time, and can be less than that amount usually used.

Inasmuch as amounts of particular active ingredients that are suitable for treating particular conditions are generally known, it is relatively easy to formulate a series of prodrugs containing a range of such active ingredients to determine the effective amount of such an active ingredient for a particular prodrug. Based upon a reading of the description herein and of the following examples, it is within the skill of the art to select an amount of any particular active ingredient and to form a prodrug as herein described for delivering an effective amount of such an active ingredient without undue experimentation. While the effective amount for all active ingredients cannot be stated, typical compositions of this invention may contain about one microgram to about one gram of active ingredient per dose administered. More preferably, a composition of this invention may contain about 1 microgram to about 250 milligrams per dose.

The examples which follow are intended as an illustration of certain preferred embodiments of the invention, and no limitation of the invention is implied.

EXAMPLE 1

Preparation of 1-Diisopropylchlorosilyl-2-[(p-chloromethyl)phenyl]ethane, Coupling with Misoprostol, and Formation of Quaternary Salt (a) Hydrosilylation of p-Vinylbenzyl Chloride with Diisopropylsilane.

Under a $N_2$ atmosphere a 250 ml round bottom flask was charged with p-vinylbenzyl chloride (31 g, 0.20 mol), diisopropylsilane (24 g, 0.20 moles); platinum divinyltetramethyldisiloxane (2.3% solution in xylene, 14 g) and 25 g of toluene. After stirring for 1 hour at room temperature, the reaction mixture was heated to 70° C. and stirred for 14 hrs. After removing the toluene by rotary evaporation the product residue was redissolved in hexane and filtered. After removing the hexane, the product was purified by eluting from silica gel with hexane. Pure product was obtained from the hexane eluent (40 g, 71%). $^1H$ and $^{13}C$ NMR, and mass spectrometry confirmed the structure of the hydrosilylated product.

(b) Chlorination of Product from (a).

The pure product from part (a) (30 g) was dissolved in 25 ml of dichloromethane and cooled to −78° C. A solution of chlorine gas in dichloromethane was slowly added to the solution at −78° C. until all of the silane was converted to the desired 1-diisopropylchlorosilyl-2-[(p-chloromethyl)phenyl]ethane. The reaction was monitored by gas chromatography. As soon as the reaction was completed, the chlorine gas was removed by sweeping the solution with $N_2$ gas. The product obtained after removal of the dichloromethane solvent had a purity >95%.

(c) Coupling with Misoprostol.

Misoprostol (0.5 g, 1.3 mmol) was dissolved in 2 ml dry DMF and then a solution of imidazole (0.175 g, 2.0 mmol) in DMF (2 ml) was added. 1-diisopropylchlorosilyl-2-[(p-chloromethyl)phenyl]ethane (452 mg, 1.5 mmol) was then added and the reaction mixture was stirred at room temperature for 14 hours. After silica chromatography using 20% hexane in ethyl acetate as an eluent, the coupled product was isolated from the eluent (0.51 g, 60%).

(d) Amination with Trimethylamine.

In a Fischer-Porter bottle, 70 mg of the product from step (c) was dissolved in THF (10 ml) and then anhydrous trimethylamine (ca. 200 mg) was added at dry ice temperature and the reaction was stirred at room temperature for 24 hours. The crude quaternized product (80 mg) was isolated by evaporation of THF. The product was purified by dissolving in dichloromethane (10 ml) and precipitating the product out of solution by the addition of diethyl ether (0.5–1 ml). TLC of the final purified product showed no free misoprostol. The structure was confirmed by FAB mass spectrometry (calc. 673.5102, obs. 673.5146), $^{29}Si$ (12 ppm); $^1H$, and $^{13}C$ NMR.

The product from 1(d) was determined to have the following structure:

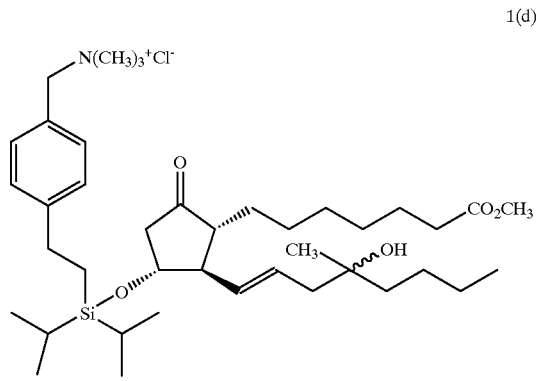

1(d)

EXAMPLE 2

Synthesis of 1-Isopropylisobutylchlorosilyl-2-[(p-chloromethyl)phenyl]ethane, Coupling with Misoprostol, and Formation of Quaternary Salt (a) Hydrosilylation of p-Vinylbenzyl Chloride with Isopropylisobutylchlorosilane.

A 1 oz. Fischer-Porter bottle was charged with dry toluene (4.82 g), isopropylisobutylchlorosilane (2.5 g, 0.0152 mol), p-vinylbenzyl chloride (2.32 g, 0.0152 mol) and (1.47 g, 2.3% solution in xylene) platinum-divinyltetramethyldisiloxane. The reaction was heated for 8 hrs. at 100° C. After removal of solvent, the product was stored in dry toluene. The yield was 72%.

(b) Coupling with Misoprostol.

To a 3 ml vial under an argon atmosphere were added misoprostol (0.4 g, 1.046 mmol), 4-dimethylaminopyridine (0.141 g, 1.15 mmol) and dichloromethane (1.0 g). Then the product from step (a) (0.398 g, 1.25 mmol) in 1.8 g dichloromethane was added. The reaction mixture was stirred for 20 hours at room temperature and then diluted with dichloromethane (50 ml) and washed with water (20 ml). The product was isolated by chromatography on silica gel using 20% hexane in ethyl acetate as an eluent.

(c) Reaction with Trimethylamine.

In a Fischer-Porter bottle, the product from step (b) (70 mg) was dissolved in THF (8 ml) and then trimethylamine (3 g) was added at −78° C. The reaction mixture was warmed to room temperature and stirred for 3 days. After removing THF the residue was washed with hexane to remove impurities. The product was characterized by high resolution mass spectrometry (calc. 669.4293, observed 669.4273) and further characterized by $^1H$, $^{13}C$ and $^{29}Si$ NMR (14.5 ppm).

The product of step 2(c) was determined to have the following structure:

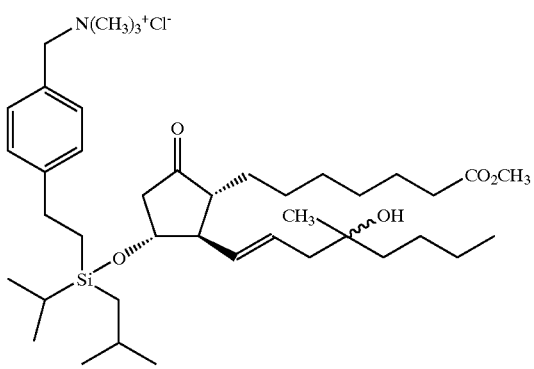

2(c)

EXAMPLE 3

Preparation of the Octyldimethylamine Quaternary Derivative of the Product from Example 1(c)

In a 50 ml round bottom flask the product from Example 1(c) (0.049 g, 0.075 mmol) and octyldimethylamine (240 mg, 10 eq.) were stirred for 4 days in 2 ml THF. The desired product was isolated by precipitation with hexane (4 ml).

The product of this example was determined to have the following structure:

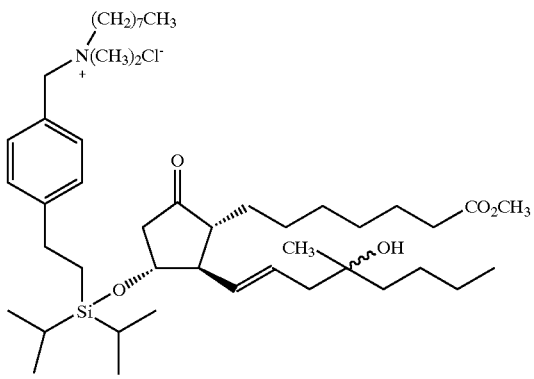

3

EXAMPLE 4

Synthesis of 1-tert-Butylphenylchlorosilyl-2-[(p-chloromethyl)phenyl]ethane, Coupling with Misoprostol, and Formation of Quaternary Salt (a) Reduction of tert-Butylphenyldichlorosilane.

To a 3 necked 100 ml round bottom flask fitted with stir bar, water cooled condenser and $N_2$ inlet adapter were added tert-butylphenyldichlorosilane (64.3 mmol) and dry diethyl ether (30 g). The solution was cooled with an ice bath and purged with $N_2$. Lithium aluminum hydride (128.6 mmol) was added and the mixture was stirred at 0° C. for 30 min, then allowed to warm to room temperature, and stirred for an additional 1.5 hours. The mixture was then allowed to reflux at 44° C. under a $N_2$ purge for 42 hrs. The reaction mixture was quenched after transferring it to a 3 necked 250 ml round bottom flask fitted with a stir bar, an addition funnel, and a $N_2$ inlet adapter. The mixture was cooled to 0° C. with an ice bath under a $N_2$ atmosphere, water (14.5 ml) was added slowly from an addition funnel, and the mixture was stirred for 30 minutes. A 15% NaOH solution (14.5 ml) was added slowly from an addition funnel and the mixture was stirred for 30 minutes.

Additional water (43.2 ml) was added slowly from an addition funnel and the mixture was allowed to warm to room temperature and stirred for 2 hours while the solution color changed from gray to white. The solids were filtered using a medium glass frit funnel and washed well with diethyl ether. The filtrate was extracted with saturated aqueous NaCl solution, then dried with magnesium sulfate. The solvents were removed by rotary evaporation and the residue dried further on a vacuum line. The yield was 95%.

(b) Hydrosilylation of 4-Vinylbenzyl Chloride.

In a dry box, a 3 oz. Fischer-Porter bottle with a stir bar and a valve top was charged with tert-butylphenylsilane (prepared in step (a), 30.4 mmol), p-vinylbenzyl chloride (30.4 mmol) and distilled toluene (17.77 g). Wilkinson's catalyst (chlorotris(triphenylphosphine)rhodium (I), 0.018 g) was added and the bottle was placed in an oil bath at 50° C. and heated for 21 hrs. The product was purified using a silica gel column (230–400 mesh) with hexane as an eluent. Two passes through silica gel were needed to obtain about 95% purity as measured by gas chromatography and NMR.

(c) Chlorination of the Product from Step 4(b).

A 100 ml round bottom flask sealed with a suba seal and containing a stir bar was charged with the product prepared in step (b) (9.6 mmol). While purging with $N_2$, anhydrous dichloromethane (60 ml) was added. The solution was then cooled with a dry ice-acetone bath. A chlorine solution was prepared by condensing chlorine in a Fischer-Porter bottle at dry ice temperature and adding anhydrous dichloromethane (1 ml $CH_2Cl_2$ per 0.1 g $Cl_2$). The chlorine solution was added to the silane solution via syringe in small portions while monitoring eaction progress by gas chromatography. The addition was continued until all of the starting silane had been converted to the chloride. Nitrogen was bubbled through the solution at room temperature to remove excess chlorine. The solution was then placed in a dry box and dichloromethane was removed by means of a vacuum line. The solution was filtered and stored in an amber vial.

(d) Misoprostol Coupling.

To a vial in a glove box which contained a stir bar were added a solution of misoprostol (1.046 mmol) in DMF (3.8 g), imidazole (2.04 mmol) and additional anhydrous DMF (3.8 g). The mixture was stirred to dissolve the reactants. The product prepared in step (c) (1.255 mmol) was added and the mixture was stirred for 96 hours. Anhydrous methanol (3.5 mmol) was added and the mixture was stirred overnight. The material from the vial was then transferred to a 125 ml separatory funnel and extracted with water (HPLC grade, 25 ml) and diethyl ether (30 ml). The aqueous layer was extracted twice with diethyl ether (30 ml). All of the ether layers were combined and extracted with saturated aqueous NaCl solution. The resulting organic phase was dried with magnesium sulfate and stripped to dryness. The desired product was isolated using a silica gel column (230–400 mesh) with 20% ethyl acetate in hexane as the mobile phase.

(e) Amination with Trimethylamine.

A 1 oz. Fischer-Porter bottle with a stir bar was charged with the product of step (d) (0.214 mmol) and anhydrous DMF (9 g). A solution of trimethylamine in anhydrous DMF (0.19 M, 2.26 ml, 2 eq) was added. The bottle was sealed and the contents stirred at room temperature overnight. The mixture was transferred to a 100 ml round bottom flask with a stir bar and dried on a vacuum line overnight to remove DMF.

The product of step 4(e) was determined to have the following structure:

4(e)

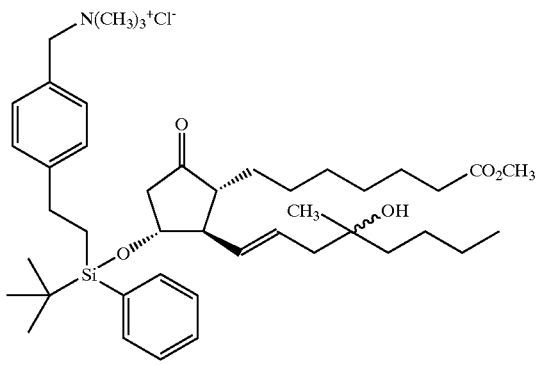

EXAMPLE 5

Synthesis of 1-(tert-Butylmethylchlorosilyl)-4-(dimethylamino)benzene, Coupling with Misoprostol, and Formation of Quaternary Salt (a) Preparation of tert-Butylmethylchlorosilane.

To a 3 necked 500 ml round bottom flask equipped with a stir bar, addition funnel, and $N_2$ inlet adapter, was added, in a dry box, dichloromethylsilane (86.9 mmol). The flask was removed from the dry box and under a $N_2$ purge, the silane was cooled to 0° C. with an ice bath. Using a canula, tert-butyllithium (1.7 M solution in pentane, 51 ml) was transferred to the addition funnel. The tert-butyllithium solution was added dropwise to the silane while stirring at 0° C. The mixture was then allowed to warm slowly and stir at room temperature overnight. The reaction mixture was analyzed by removing a small sample, extracting it with water and diethyl ether, drying, and obtaining an NMR spectrum, which showed that the reaction was complete.

(b) Preparation of 4-Dimethylaminophenyllithium and coupling with tert-Butylmethylchlorosilane.

A 250 ml 3 necked round bottom flask equipped with a stir bar was charged with finely cut lithium wire (in mineral oil, ca. 1% sodium, 0.2 moles) and diethyl ether (87 g) in a dry box. The flask was then fitted with an addition funnel, a water-cooled condenser, and an argon inlet adapter. Into a large bottle were weighed 4-bromo-N,N-dimethylaniline (86.9 mmol) and diethyl ether (17.4 g). The resulting solution was placed in an addition funnel. The bottle was rinsed with additional diethyl ether (12.6 g) which was also added to addition funnel. The flask was removed from the dry box. While purging the flask with argon and stirring, the aniline solution was slowly added to the lithium-ether mixture. The mixture was stirred for 30 min. after addition was complete, then refluxed (44° C.) for 2.5 hours, cooled, and transferred to an addition funnel. The contents of the addition funnel were added dropwise to the tert-butylmethylchlorosilane (prepared in step (a)) at 0° C. The reaction mixture was allowed to warm slowly to room temperature, then stirred at room temperature overnight. The reaction mixture was poured into saturated aqueous $NH_4Cl$ (300 ml) that had been chilled with ice in a 500 ml separatory funnel. The contents were shaken thoroughly and allowed to separate. The ether layer was removed and set aside. The aqueous layer was extracted two more times with 200 ml portions of ether. All ether layers were combined and extracted once with saturated aqueous NaCl solution. The ether layer was then dried with magnesium sulfate. The drying agent was removed by filtration, evaporated to dryness, and dried on a vacuum line. The greenish-brown solid product was dissolved in diethyl ether, treated with 1 g of decolorizing carbon, and stirred at 30–35° C. After filtration to remove the carbon, the filtrate was stripped to dryness using a rotary evaporator. The residue was redissolved in ethanol (150 ml) and placed in a 600 ml beaker with a stir bar. Water (50 ml) was added slowly from a separatory funnel, causing the product to precipitate from the solution. The product was collected and redissolved in ethanol and the precipitation with water repeated. The clean product was dissolved in diethyl ether (100 ml) and extracted with saturated NaCl solution. The ether layer was dried with magnesium sulfate. The drying agent was removed by filtration followed by removal of the solvent by evaporation on a rotary evaporator, and then the residue was dried on a vacuum line. The white product was analyzed by NMR, GC, and mass spectrometry and determined to be 1-(tert-butylmethylsilyl)-4-(dimethylamino)benzene.

(c) Chlorination.

Into a 100 ml round bottom flask with a stir bar were placed the product prepared in step (b) (2.26 mmol) and 5% Pd/C (dry, 96 mg, 0.02 eq) and the flask placed into a dry box. Distilled toluene (3 g) was added, and the contents stirred to mix well. Acetyl chloride (2.26 mmol) was added dropwise. The reaction was rapid and complete within minutes. The mixture was filtered to remove catalyst using a medium glass frit funnel. The filtrate was evaporated on a vacuum line and analyzed by NMR and mass spectrometry which confirmed the production of 1-(tert-butylmethylchlorosilyl)-4-(dimethylamino)benzene.

(d) Misoprostol Coupling.

Misoprostol (1.046 mmol) was weighed into a vial with a stir bar and the vial placed into a dry box. Imidazole (2.04 mmol) and anhydrous DMF (3.8 g) were added and the mixture stirred to dissolve the contents. In a separate vial were weighed the chlorosilane prepared in step (c) (1.26 mmol) and anhydrous DMF (2 g). This solution was added to the solution in the first vial, and the second vial was washed with anhydrous DMF (1.8 g) which was also added to the first vial. The reaction mixture was stirred at room temperature in a dry box. After 23.5 hours, the contents were transferred to a 125 ml separatory funnel and extracted with HPLC grade water (25 ml) and diethyl ether (30 ml). The aqueous layer was extracted twice with diethyl ether (25 ml). All ether layers were combined and extracted once with saturated aqueous NaCl solution. The ether layer was dried with magnesium sulfate and stripped to dryness using a rotary evaporator. The desired product was isolated using a Waters Delta Prep 4000 (2 columns 40×200 mm) and 80% HPLC hexane/20% HPLC ethyl acetate as the mobile phase. NMR and mass spectrometry were used to verify the product structure.

(e) Quaternization with Methyl Iodide.

A 1 oz. Fischer-Porter bottle with a stir bar was charged with the product prepared in step (d) (0.851 mmol) and anhydrous DMF (6 ml). Methyl iodide (1.702 mmol) was added and the bottle was sealed and stirred at room temperature for 3 days. The contents were then transferred to a 50 ml round bottom flask with a stir bar and dried on a vacuum line.

(f) Chloride-iodide Exchange.

Into a 250 ml r.b. flask with stir bar were placed the product prepared in step (e) (0.887 mmol), dry acetone (65 ml), and silver chloride (8.87 mmol). The mixture was stirred at room temperature overnight. The mixture was filtered using a medium glass frit funnel and the filtrate stripped to dryness using a rotary evaporator. Some solids still remained in the residue, which was issolved in anhydrous methanol (25 ml), stirred for 30 min., and filtered with a fine glass frit funnel. The filtrate was stripped to dryness using a rotary evaporator, and dried on a vacuum line. The residue was dissolved in 2 ml diethyl ether and precipitated by addition of anhydrous hexane (1 ml). This precipitation was repeated twice, and then the product was dissolved in ether, stripped to dryness, and dried on a vacuum line overnight. The structure of the product was confirmed by NMR and mass spectrometry.

The product of step 5(f) was determined to have the following structure:

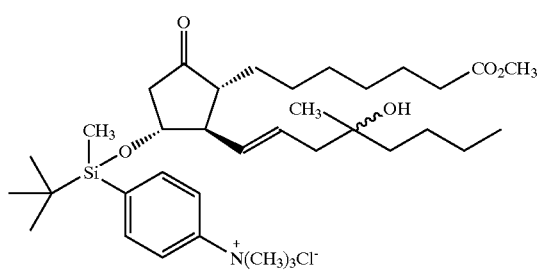

5(f)

EXAMPLE 6

Synthesis of 1-(Isobutylisopropylchlorosilyl)-2-[(p-chloromethyl)phenyl]ethane, Coupling with Misoprostol, and Formation of Quaternary Salt (a) Hydrosilylation.

A 3 oz. Fischer-Porter bottle with a stir bar and a valve top was placed in a dry box and charged with p-vinylbenzyl chloride (16.38 mmol), isobutylisopropylchlorosilane (16.38 mmol), and distilled toluene (5.2 g), and stirred to mix well. Platinum divinyltetramethyldisiloxane (2–3% Pt complex in xylene, 1.59 g). The reactor was sealed, removed from the dry box, and placed in a 100° C. oil bath and heated for 7 hours. The reactor was then placed back into the dry box. Decolorizing carbon was added to the solution, which was stirred for 30 min., and then filtered through celite on a fine glass frit funnel. The filtrate was evaporated on a vacuum line and the structure of the product was confirmed by NMR.

(b) Coupling Chlorotriethylsilane to Misoprostol at C-11.

Into a 25 ml round bottom flask in a dry box were weighed misoprostol (1.76 mmol) and anhydrous DMF (3 g). A solution of imidazole (2.64 mmol) in anhydrous DMF (2 g) was added, followed by a solution of chlorotriethylsilane (1.76 mmol) in anhydrous DMF (2.6 g). The mixture was stirred at room temperature for 3.5 hrs., then removed from the dry box, and the material was transferred to a separatory funnel with 20 ml HPLC water and 20 ml diethyl ether. The aqueous layer was extracted twice with ether. All ether layers were combined and extracted with two 40 ml portions of HPLC grade water. The ether layer was dried with magnesium sulfate, filtered, and the filtrate stripped to dryness using a rotary evaporator. The desired product was isolated using a silica column (230–400 mesh) with 80% HPLC hexane/20% HPLC ethyl acetate as the mobile phase. The structure of the product was confirmed by NMR.

(c) Coupling of Step (a) Product to Step (b) Product.

Into a vial with a stir bar was weighed the product prepared in step (b) (0.403 mmol). The vial was placed into a dry box. Imidazole (0.605 mmol) and anhydrous dichloromethane (0.369 g) were added. The contents were stirred until dissolved. The silane linker prepared in step (a) (0.403 mmol) was added and the mixture was stirred at room temperature for 102 hours, then removed from the dry box, and the material transferred to a separatory funnel with 10 ml diethyl ether and 10 ml HPLC water. The aqueous layer was extracted twice with diethyl ether (10 ml). All ether layers were combined and extracted once with HPLC grade water. The ether layer was dried with magnesium sulfate, filtered, and the filtrate stripped to dryness using a rotary evaporator. The residue was redissolved with distilled THF (11 g), 0.1 N HCl (2 ml) was added, and the mixture was stirred for 75 min., and the material transferred to a separatory funnel with 10 ml diethyl ether and 10 ml HPLC water. The aqueous layer was extracted twice with ether. All ether layers were combined and extracted once with HPLC grade water. The ether layer was dried with magnesium sulfate, filtered, and the filtrate stripped to dryness using a rotary evaporator. Product was isolated using a silica gel column (230–400 mesh) with 80% hexane/20% ethyl acetate as the mobile phase. The structure of the product was confirmed by NMR.

(d) Amination with Trimethylamine.

A 1 oz. Fischer-Porter bottle with a stir bar and a valve top was charged with a solution of the product from step (c) in distilled THF (6 g). The contents were chilled with dry ice. Trimethylamine gas was bubbled through the solution. The contents were allowed to warm to room temperature and stirred at room temperature for 65 hrs. The bottle was vented and purged well with $N_2$. The contents were transferred to a 100 ml round bottom flask and stripped to dryness using a rotary evaporator. Anhydrous hexane (3 ml) was added and the mixture shaken on a wrist shaker for 15 min. The supernatant was decanted, and the hexane extraction repeated three times. The cleaned product was dried. Only 13 mg of product was obtained. The structure of the product was confirmed by NMR.

The product of step 6(d) was determined to have the following structure:

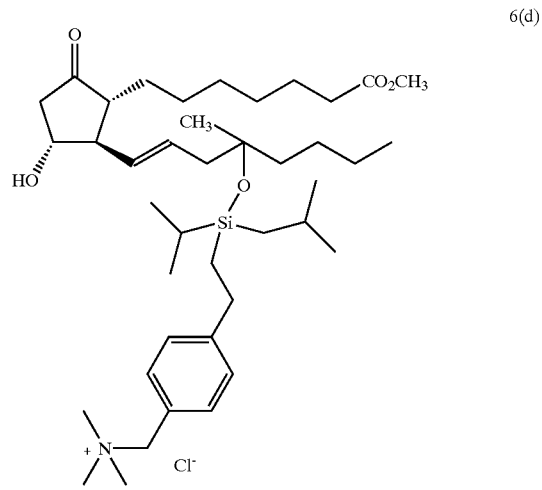

6(d)

Rate data for in-vitro release of misoprostol from various prodrugs, some of whose syntheses are illustrated in the examples, were obtained and are displayed in Table 1.

TABLE 1

Release Rates for $R^1R^2R^3Si$-O-misoprostol

| Example No. | $R^1$ | $R^2$ | $R^3$ | attach. site | $k_{obs}$ (%/min.) |
|---|---|---|---|---|---|
|  | $(CH_3)_3N^+CH_2Ph(CH_2)_2$ | Ethyl | Ethyl | C-16 | 1.296 |
| 2(c) | $(CH_3)_3N^+CH_2Ph(CH_2)_2$ | iso-Propyl | iso-Butyl | C-11 | 0.66 |
| 6(d) | $(CH_3)_3N^+CH_2Ph(CH_2)_2$ | iso-Propyl | iso-Butyl | C-16 | 0.643 |
| 1(d) | $(CH_3)_3N^+CH_2Ph(CH_2)_2$ | iso-Propyl | iso-Propyl | C-11 | 0.105 |

The release rates set forth in Table 1 were determined in 4 ml of 0.001 N aqueous HCl+1.5 ml acetonitrile+0.5 ml of 0.1–0.8 mg substrate/ml acetonitrile. The rate data were usually obtained between 0 and 25% conversion levels. The reaction was monitored by HPLC by studying the appearance of misoprostol.

EXAMPLE 7

Coupling of Shearwater™ PEG3500 to 1-Isopropylisobutylchlorosilyl-2-[(p-chloromethyl)phenyl]ethane-Misoprostal System In a 50 ml round bottom flask, the product from Example 1(c) (0.367 g, 0.565 mmol), was stirred in 2 ml of dry DMF with a stir bar. After mixing, 0.4945 g of Shearwater™ 3500 MW amino-terminated PEG was added. Next, diisopropyl-ethylamine (0.083 g, 0.565 mmol) and 2 ml DMF were added and stirred, followed by potassium iodide (0.094 g, 0.565 mmol). The solution was heated to 35° C.

The reaction was monitored by TLC by studying the disappearance of the product of Example 1(c). The reaction was allowed to proceed a total of 68 hours.

The DMF was then removed by vacuum line, and the remaining product was dissolved in THF and filtered through a 1 μm filter. The desired product was then removed by repeated precipitation with hexane five times to remove monomer impurities.

The precipitated polymer was dried overnight and the coupling of the PEG group to the misoprostol system was confirmed by NMR and molecular weight analysis.

Release rate data for the product of Example 7 are shown in Table 2.

EXAMPLE 8

Coupling of Shearwater™ PEG10,000 to 1-Isopropylisobutylchlorosilyl-2-[(p-chloromethyl)phenyl]ethane-Misoprostol Systems The Shearwater™ PEG10,000 was added to the product of Example 1(c) as described in Example 7, except with a greater amount of DMF (14 ml total).

The precipitated polymer was dried overnight and the coupling of the PEG group to the misoprostol system was confirmed by NMR and molecular weight analysis.

Release data for the product of Example 8 are shown below.

TABLE 2

Comparison Release Rates of PEG to 1-isopropyl-isobutylchlorosilyl-2-[(p-chloromethyl)phenyl]ethane-Misoprostol Systems

| Example No. | Coupled PEG Group | pH 1.4 at 0.5 hours | pH 1.4 at 3 hours |
|---|---|---|---|
| 5(f) | None | 63% | >80% |
| 7 | Shearwater™ PEG3,500 | 10.44% | 28% |
| 8 | Shearwater™ PEG10,000 | 22% | 48% |

The release rates set forth in Table 2 were determined by mixing 750 μl of pH 1.4 buffer and 100 μl of the test solution (2 mg substrate/ml) into a vial. The vial was shaken and at various intervals, 100 μl of the solution removed and monitored by HPLC for the appearance of misoprostol.

Table 2 compares the respective rates of drug delivery systems comprising PEG to those without at pH 1.4. There was no detectable misoprostol release any of the examples at pH>4.0.

The delivery systems comprising PEG at pH 1.4 substantially lowers the release rate of misoprostol in comparison to systems without PEG. Furthermore, the lower molecular weight PEG systems (3,500 mw PEG) manifested a significantly slower release rate than the larger PEG-misoprostol systems (10,000 mw).

Other variations and modifications of this invention will be obvious to those skilled in the art. This invention is not limited except as set forth in the claims.

What is claimed is:

1. A compound of the formula

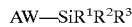
$$AW-SiR^1R^2R^3$$

wherein $R^1$ and $R^2$ are independently alkyl, cycloalkyl, alkenyl, alkynyl, aryl, aralkyl, alkaryl, or a hydrophilic group; $R^3$ is a hydrophilic group; and AW is the covalently bonded form of a drug AWH, wherein W is O, NH, S, or an enolate group, and wherein said drug AWH is selected from the group consisting of prostaglandins and prostacyclins, and wherein at least one of $R^1$, $R^2$ or $R^3$ comprises a hydrophilic group that contains a polyol moiety.

2. The compound of claim 1, wherein $R^1$ and $R^2$ are independently alkyl, cycloalkyl, alkenyl, alkynyl, aryl, aralkyl or alkaryl.

3. The compound of claim 2, wherein $R^3$ is a group containing at least two quaternary ammonium salts and at least two $AW\text{-}SiR^1R^2$ groups.

4. The compound of claim 2, wherein the compound comprises more than one type of drug AW.

5. The compound of claim 1, wherein $R^3$ is a group with the formula

$$-L-(NR^4R^5R^6)^+X^-$$

wherein $X^-$ is a halide ion or any pharmaceutically acceptable anion; L is a difinctional alkyl, alkenyl or alkynyl group, a polyol moiety, or a group with the formula

$$(CH_2)_m-Ar-(CH_2)_n$$

wherein Ar is a difunctional aryl or cycloalkyl group, m is an integer from 0 to 3 inclusive, and n is an integer from 0 to 2 inclusive; $R^4$ and $R^5$ are independently alkyl, alkenyl, alkynyl or a polyol moiety; and $R^6$ is alkyl, alkenyl, alkynyl, a polyol moiety, or a group with the formula —B—(NR⁴R⁵)⁺—L—SiR¹R²WA X⁻ wherein —B— is a difunctional alkyl, alkenyl, or alkynyl group, a polyol moiety, or a group with the formula (CH₂)ⱼ—Ar—(CH₂)ₖ wherein j is an integer from 0 to 3 inclusive, and k is an integer from 0 to 3 inclusive.

6. The compound of claim 5, wherein L or B is a polyol moiety.

7. The compound of claim 6, wherein the polyol moiety is polyethylene glycol moiety.

8. The compound of claim 1, wherein the polyol moiety is a polyethylene glycol moiety.

9. The compound of claim 8, wherein the polyol moiety has the formula NH₂(CH₂CH₂O—CH₂CH₂O)ₖ, wherein k is an integer in the range of 1 to 100.

10. The compound of claim 9, wherein k is an integer in the range of 10 to 50.

11. A method for preparing a compound of the formula

AW—SiR¹R²R³ wherein R¹ and R² are independently alkyl, cycloalkyl, alkenyl, alkynyl, aryl, aralkyl, alkaryl or a hydrophilic group which is a polyol moiety; R³ is a hydrophilic group; and AW is the covalently bonded form of a drug AWH, wherein W is O, NH, S, or an enolate group and wherein the drug AWH is a prostaglandin or a prostacyclin; said method comprising the steps of:

(a) reacting the drug AWH with a compound of formula

YSiR¹R²R⁷ wherein Y is halo, or an alkyl-, haloalkyl-, aryl-, alkaryl-, aralkyl-, or haloaryl-sulfonate ester; and R⁷ is substituted by a halo group to form a compound of formula AWSiR¹R²R⁷; and (b) reacting a product of step (a) with a compound containing at least one amino group or with a polyol to produce the compound of formula AW—SiR¹R²R³;

wherein at least one of R¹, R² or R³ comprises a hydrophilic group which is a polyol moiety.

12. The method according to claim 11, wherein the polyol moiety is a polyethylene glycol moiety.

13. The method according to claim 12, wherein the compound containing at least one amino group contains a tertiary amine.

14. The method according to claim 13, wherein R³ is a group with the formula

—L—(NR⁴R⁵R⁶)⁺X⁻ wherein X⁻ is a halide ion or any pharmaceutically acceptable anion and L is a difunctional alkyl, alkenyl or alkynyl group, a polyol moiety, or a group with the formula (CH₂)ₘ—Ar—(CH₂)ₙ wherein Ar is a difunctional aryl or cycloalkyl group, m is an integer from 0 to 3 inclusive, n is an integer from 0 to 2 inclusive; and the compound containing at least one tertiary amino group has the formula Z(NR⁴R⁵)ₚ, wherein R⁴ and R⁵ are independently an alkyl, alkenyl, alkynyl or polyol moiety; and R⁶ is an alkyl, alkenyl, alkynyl, polyol moiety or a group with the formula —B—(NR⁴R⁵)⁺—L—SiR¹R²WA X⁻ wherein —B— is a difunctional alkyl, alkenyl, alkynyl or a polyol group, or a group with the formula (CH₂)ⱼ—Ar—(CH₂)ₖ wherein j is an integer from 0 to 3 inclusive, and k is an integer from 0 to 3 inclusive.

15. The method according to claim 14, wherein L or B comprises a polyol moiety.

16. The method according to claim 11, wherein R³ comprises a polyol moiety.

17. The method of claim 11 wherein R⁷ is a group of formula

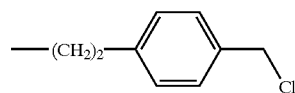

18. The method according to either of claim 16 or 17, wherein the polyol moiety is an amino-substituted polyol moiety.

19. The method according to either of claim 16 or 17, wherein the compound containing at least one amino group is an alkylamine comprising twenty carbons or less.

20. The method according to claim 19, further comprising a step of reacting with a transformed polyol to provide an amine-substituted polyol.

21. The method according to claim 20, wherein the amine-substituted polyol is represented by the formula R⁸(CH₂CH₂O—CH₂CH₂)ₖNH₂ wherein R⁸ is an alkoxy, amino, hydroxyl or hydrogen group, and k is an integer in the range of 1–100.

22. The method according to claim 16 or 17, wherein the polyol moiety is an unmodified polyol moiety.

23. The method according to claim 22, further comprising a step of transforming the unmodified polyol to produce a transformed polyol.

24. The method according to claim 23, further comprising a step of reacting the transformed polyol with a tertiary amine.

25. The method of claim 11 wherein the drug AWH is a prostaglandin or a prostacyclin.

26. The method of claim 25 wherein the prostaglandin is misoprostol.

27. A method of treatment for gastric ulcers comprising administering the compound of claim 1 to a human suffering therefrom.

28. A method for prevention of gastric ulcers comprising administering the compound of claim 1 to a human.

* * * * *